US007111975B2

(12) United States Patent
Fenton et al.

(10) Patent No.: US 7,111,975 B2
(45) Date of Patent: Sep. 26, 2006

(54) APPARATUS AND METHODS FOR MOVING A WORKING FLUID BY CONTACT WITH A TRANSPORT FLUID

(75) Inventors: Marcus B. M. Fenton, St Neots (GB); Philip A. Kitchen, Royston (GB); Michael T. Todman, Warwickshire (GB); Alexander G. Wallis, Berkhamstead (GB)

(73) Assignee: Pursuit Dynamics plc, Royston (GB)

( * ) Notice: Subject to any disclaimer, the term of this patent is extended or adjusted under 35 U.S.C. 154(b) by 342 days.

(21) Appl. No.: 10/477,708

(22) PCT Filed: Oct. 10, 2003

(86) PCT No.: PCT/GB03/00440

§ 371 (c)(1),
(2), (4) Date: Nov. 14, 2003

(87) PCT Pub. No.: WO2004/033920

PCT Pub. Date: Apr. 22, 2004

(65) Prior Publication Data

US 2004/0141410 A1     Jul. 22, 2004

(30) Foreign Application Priority Data

Oct. 11, 2002    (GB)  ................. 0223572.9
Nov. 20, 2002    (GB)  ................. 0227053.6
Jan. 20, 2003    (GB)  ................. 0301236.6

(51) Int. Cl.
    *B01F 5/04*       (2006.01)
    *F04F 5/46*       (2006.01)

(52) U.S. Cl. .................................. 366/163.2; 137/889
(58) Field of Classification Search ............. 366/163.1, 366/163.2, 167.1, 173.1, 174.1, 176.1; 48/189.4; 137/888–890
See application file for complete search history.

(56) References Cited

U.S. PATENT DOCUMENTS 2,396,290 A   *   3/1946   Schwarz (Continued)

FOREIGN PATENT DOCUMENTS

DE           3316233 A1   *   11/1984

(Continued)

*Primary Examiner*—Charles E. Cooley
(74) *Attorney, Agent, or Firm*—Nixon & Vanderhye, P.C.

(57) ABSTRACT

A fluid mover (1) includes a passage (3) of substantially constant cross section into which supersonic steam is injected through an annular nozzle (16) as a transport fluid to contact a working fluid, e.g. a liquid, to be treated, the passage further including a mixing chamber (3A) downstream of the steam injection where the mixture is accelerated upon the creation of a low pressure zone occasioned by the condensation of the steam, a dispersed droplet regime and a shock wave being generated downstream of the nozzle (16). A pseudo-convergent/divergent section is created and provides a flexible boundary in the absence of physical constraints to yield an improved performance by combining shear dispersion and/or disassociation with the effects of the shock wave. The fluid mover (1) may be used in a wide variety of applications for pumping, heating, mixing, disintegrating, classifying and separating among others.

45 Claims, 4 Drawing Sheets

U.S. PATENT DOCUMENTS

Figure 1:
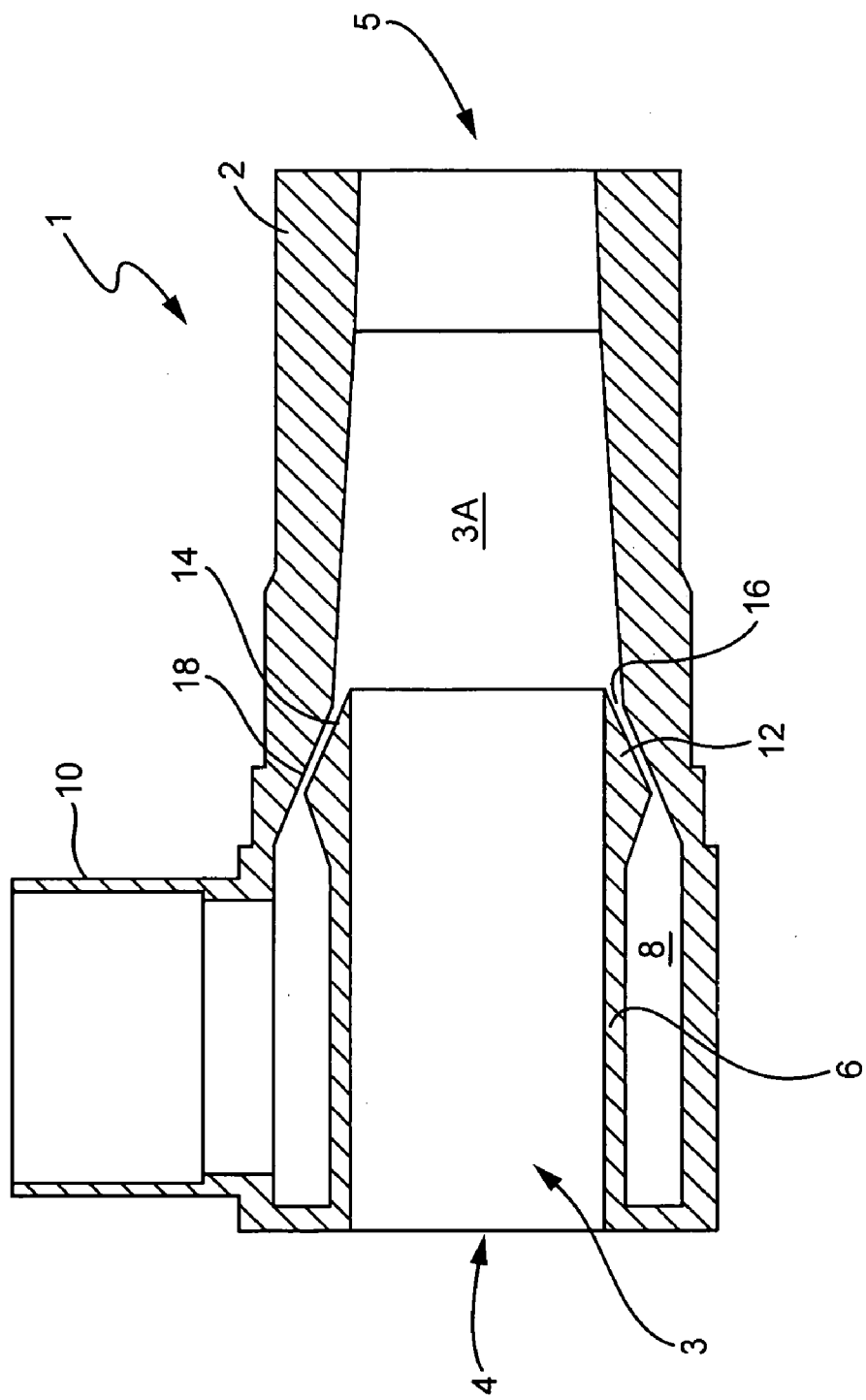

| | | | |
|---|---|---|---|
| 3,304,564 A * | 2/1967 | Green et al. |
| 3,664,768 A * | 5/1972 | Mays et al. |
| 3,799,195 A * | 3/1974 | Hermans |
| 4,101,246 A * | 7/1978 | Erickson |
| 4,157,304 A * | 6/1979 | Molvar |
| 4,487,553 A * | 12/1984 | Nagata |
| 5,171,090 A * | 12/1992 | Wiemers |
| 5,338,113 A * | 8/1994 | Fissenko |
| 5,544,961 A | 8/1996 | Fuks et al. |
| 5,857,773 A * | 1/1999 | Tammelin |
| 5,863,128 A * | 1/1999 | Mazzei |
| 6,456,871 B1 * | 9/2002 | Hsu et al. |
| 6,523,991 B1 | 2/2003 | Maklad |
| 6,623,154 B1 * | 9/2003 | Garcia |
| 6,802,638 B1 * | 10/2004 | Allen |
| 6,830,368 B1 * | 12/2004 | Fukano |
| 7,029,165 B1 * | 4/2006 | Allen ................... 366/163.2 |
| 2004/0141410 A1 * | 7/2004 | Fenton et al. |

FOREIGN PATENT DOCUMENTS

| | | | |
|---|---|---|---|
| EP | 282061 A2 | * | 9/1988 |
| EP | 0889244 A2 | * | 1/1999 |
| GB | 1227444 | * | 4/1971 |
| GB | 2207952 A | * | 2/1989 |
| GB | 2 242 370 A | | 10/1991 |
| GB | 2 313 410 | | 11/1997 |
| JP | 4-184000 | * | 6/1992 |
| JP | 10-141299 | * | 5/1998 |
| RU | 2040322 C1 | * | 7/1995 |
| WO | 89/07204 | * | 8/1989 |
| WO | 89/10184 | * | 11/1989 |
| WO | 2004/033920 A1 | * | 4/2004 |

* cited by examiner

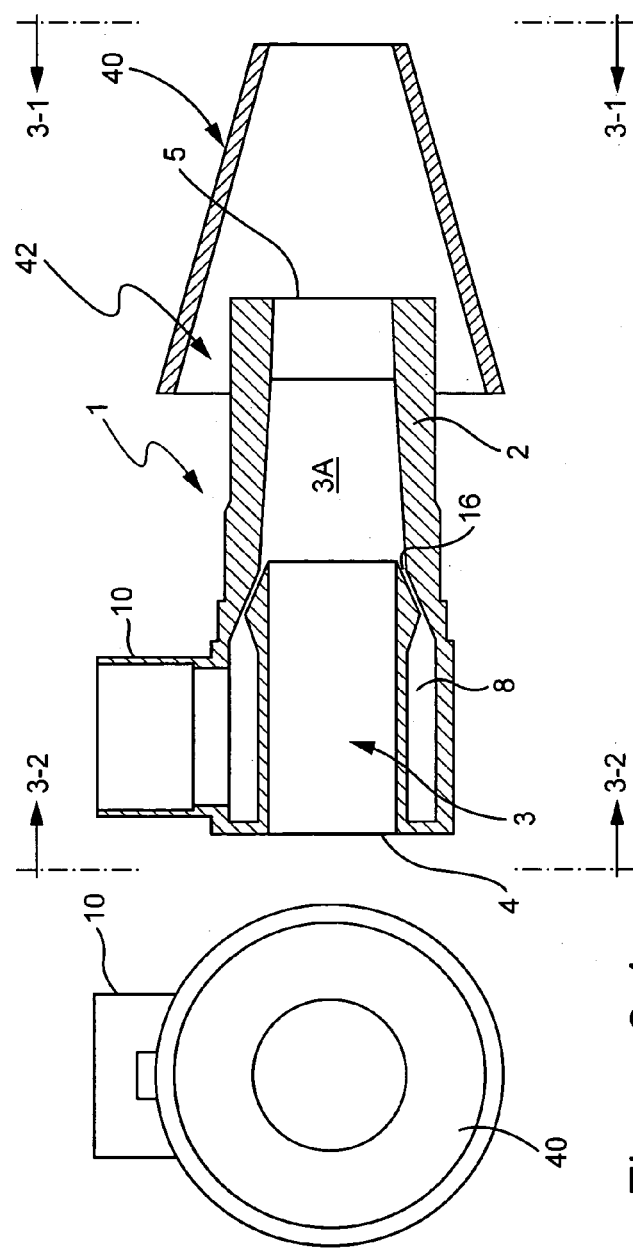

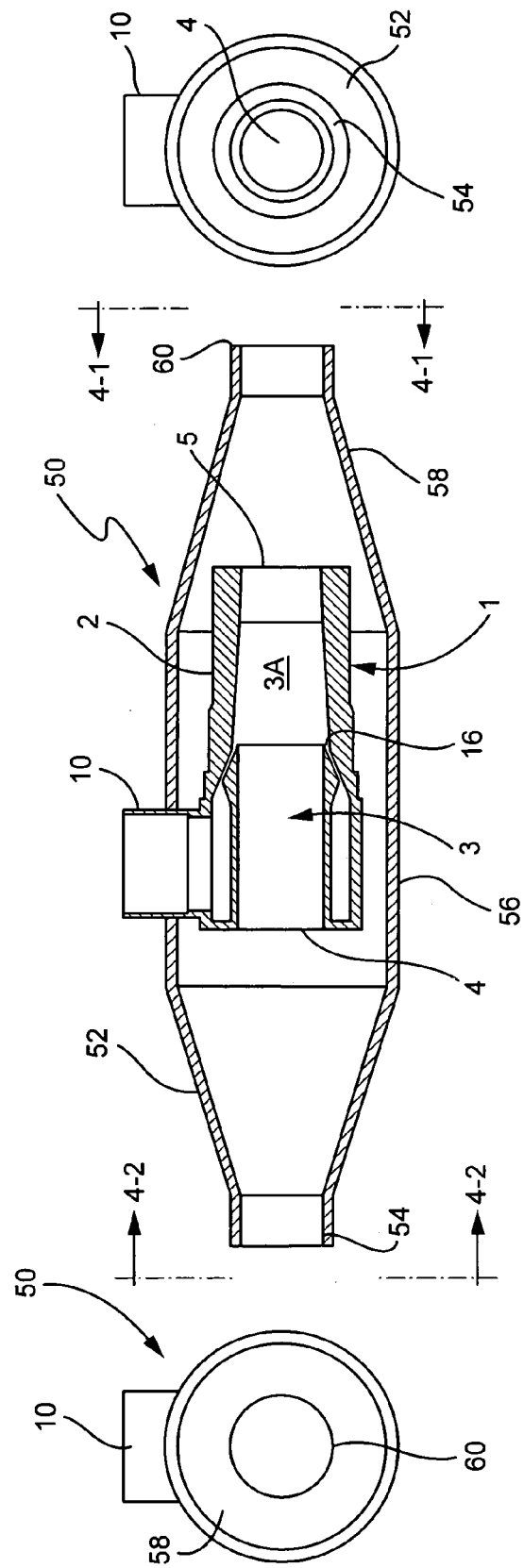

APPARATUS AND METHODS FOR MOVING A WORKING FLUID BY CONTACT WITH A TRANSPORT FLUID

This application is the U.S national phase of international application PCT/GB03/004400 filed 10 Oct. 2003 which designated the U.S.

FIELD OF INVENTION

This invention relates to a fluid mover.

BACKGROUND AND SUMMARY OF THE INVENTION

The present invention has reference to a fluid mover having a number of practical applications of diverse nature ranging from marine propulsion systems to pumping applications for moving and/or mixing fluids and/or solids of the same or different characteristics. The present invention also has relevance in the fields inter alia of heating, cleaning, aeration, gas fluidisation, and agitation of fluids and fluids/solids mixtures, particle separation, classification, disintegration, emulsification, homogenisation, dispersion, hydration, atomisation, droplet production, viscosity reduction, density reduction, and pasteurisation More particularly the invention is concerned with the provision of a fluid mover having essentially no moving parts Ejectors are well known in the art for moving working or process fluids by the use of a either a central or an annular jet which emits steam into a duct in order to move the fluids through or out of appropriate ducting or into or through another body of fluid. The ejector principally operates on the basis of inducing flow by creating negative pressure, generally by the use of the venturi principle. The majority of these systems utilise a central steam nozzle where the induced fluid generally enters the duct orthogonally to the axis of the jet, although there are exceptions where the reverse arrangement is provided. The steam jet is accelerated through an expansion nozzle into a mixing chamber where it impinges on and is mixed with process fluid. The mixture of process fluid and steam is accelerated to higher velocities within a downstream convergent section prior to a divergent section, e.g. a venturi. The pressure gradient generated in the venturi induces new process fluid to enter the mixing chamber. The energy transfer mechanism in most steam ejector systems is a combination of momentum, heat and mass transfer but by varying proportions. Many of these systems employ the momentum transfer associated with a converging flow, while others involve the generation of a shock wave in the divergent section. One of the major limitations of the conventional convergent/divergent systems is that their performance is very sensitive to the position of the shock wave which tends to be unstable, easily moving away from its optimum position. It is known from the prior art mentioned infra that if the shock wave develops in the wrong place within the convergent/divergent sections, the relevant unit may well stall. Such systems can also only achieve a shock wave across a restricted section.

Furthermore, for systems which employ a central steam nozzle, the throat dimension restriction and the sharp change of direction affecting the process fluid presents a serious limitation on the size of any particulate throughput and certainly any rogue material that might enter the system could cause blockage.

U.S. Pat. No. 2,396,290 to Schwarz discloses a sludge system intended essentially as an apparatus for removing from storage tanks the accumulation of viscous tar or semi-fluid tar, oil sludges and the like. The Schwarz system has a throat body provided with an outwardly flared portion at one end, a steam intake nozzle extending into the body and having a central opening for the passage of material therethrough into the throat body, and a steam discharge nozzle at the flared end for drawing material out of the flared portion of the throat body. The principal objective of Schwarz is to provide a means whereby the difficult materials recited above may be fluidised by a combination of the impact of the steam initially at the intake end of the throat body and the heat of the steam, the material being further subjected to the same action afforded by the discharge nozzle. The viscosity of the difficult material is thus reduced to improve flowability to allow pumping. It is to be noted that the flow of material whilst being assisted through the throat body has to pass from a wide bore nipple into a tapered section prior to the location of the primary steam nozzle, thus constraining the material and potentially causing blockages. Equally the throat body is of smaller dimension than the intake nipple and the tapered section, thus combining to create a constriction to the flow, albeit that the intention is to provide a concentration of impact and heat application for the purpose taught. The secondary or discharge nozzle fulfils a similar function to that of the primary nozzle to give a second stage impact and fluidising effect to the flowing material thus to enhance induction of the material through the system. The potential disadvantage of the Schwarz system is that by virtue of the convergent nature of the inlet to the unit and the constricted throat portion the free flow of fluid materials therethrough is likely to be difficult or restricted by the physical characteristics of the materials. As will be appreciated control on the type and size of material entering this system is difficult and the chances of blockage are high from material or agglomerates which have a size approaching the inlet bore size of the unit.

Canadian Patent No 833 980 to Schutte and Koerting Co is concerned with a jet pump of the type having a compressible flow in the diffusor and a supercritical ratio of suction to discharge pressures. The method and apparatus described by Schutte and Koerting are aimed at overcoming certain defined disadvantages associated with the operation of jet pumps in which supersonic velocities initially prevail in the mixture of the motive or thrust stream and the suction stream. As is explained in this prior art the change from supersonic to subsonic velocity occurs in a shock zone. In particular the problem associated with this type of pump, used for pumping gas, resides in controlling the positioning of the shock wave which is critical in that if it moves into either the intake or the discharge zone of the diffusor, significant difficulties arise. In particular, if the shock wave moves into the convergent conical intake zone the jet pump becomes unstable and might even fail. If the shock wave moves into the divergent conical exit zone the rate of flow of the mixture of the thrust and suction streams is accelerated resulting in a reduction in efficiency. The patentees propose a method of monitoring the prevailing conditions within the diffusor and to vary the thrust stream accordingly in order to position the shock wave accurately thereby to optimise efficiency. The jet pump of this prior art is essentially a conventional steam ejector and the invention merely lies in the monitoring and control of the shock wave positioning. This jet pump is configured for gas pumping and as such would be unsuitable for pumping liquids or liquid/solids mixtures, not least because of the significant difficulties associated with achieving supersonic velocities with substantially incompressible fluids. Clearly the amount of energy that would be required to impart supersonic velocity to the mixture would be prohibitive since the performance would be poor.

U.S. Pat. No. 3,664,768 to Mays concerns a fluid transformer of the straight-through type for sludges and other liquid/solids materials in which again the throat area converges, in this instance in a stepwise configuration thereby giving rise to potential impaction of the solids elements of the fluids passing therethrough. It is to be noted that Mays is silent regarding the nature of the impelling fluid.

An object of the present invention is to provide a fluid mover having essentially no moving parts having an improved performance than fluid movers currently available in the absence of any constriction such as is exemplified in the prior art herein recited.

A further object of the present invention is to provide a method of moving fluid.

According to a first aspect of the present invention a fluid mover includes a hollow body provided with a straight-through passage of substantially constant cross section with an inlet at one end of the passage and an outlet at the other end of the passage for the entry and discharge respectively of a working fluid, a nozzle substantially circumscribing and opening into said passage intermediate the inlet and outlet ends thereof, an inlet communicating with the nozzle for the introduction of a transport fluid, a mixing chamber being formed within the passage downstream of the nozzle, the nozzle being so disposed and configured that in use a dispersed droplet flow regime and a supersonic shock wave are created within the mixing chamber by the introduction and condensation of the transport fluid.

The transport fluid is preferably a condensable fluid and may be a gas or vapour, for example steam, which may be introduced in either a continuous or discontinuous manner.

According to a second aspect of the present invention a fluid mover includes a hollow body provided with a straight-through passage of substantially constant cross section having an inlet at one end of the passage and an outlet at the other end of the passage for the entry and discharge respectively of a working fluid, a steam nozzle substantially circumscribing and opening into said passage intermediate the inlet and the outlets thereof, a steam inlet communicating with the nozzle for the introduction of steam, a mixing chamber being formed in the passage downstream of the nozzle, the nozzle being so disposed and configured that in use a dispersed droplet flow regime and a supersonic shock wave are created in the mixing chamber by the introduction and condensation of steam.

At or near the point of introduction of the transport fluid, for example immediately downstream thereof, a pseudo-vena contracta or pseudo convergent/divergent section is generated, akin to the convergent/divergent section of conventional steam ejectors but without the physical constraints associated therewith since the relevant section is formed by the effect of the steam impacting upon the working or process fluid. Accordingly the fluid mover of the present invention is more versatile than conventional ejectors by virtue of a flexible internal boundary. The flexible boundary lies between the working fluid at the center and the solid wall of the unit, and allows disturbances or pressure fluctuations in the multi phase flow to be accommodated better than for a solid wall. This advantageously reduces the sonic velocity within the multi phase flow, resulting in better droplet dispersion, increasing the momentum transfer zone length, thus producing a more intense shockwave. Accordingly the positioning and intensity of the shock wave is variable depending upon the specific requirements of the system in which the fluid mover is disposed.

The mechanism of the present invention relies on a combination of effects in order to achieve its high versatility and performance, notably heat, momentum and mass transfer which gives rise to the generation of the shock wave and also provides for shearing of the working fluid flow on a continuous basis by shear dispersion and/or disassociation.

The intensity of the supersonic shock wave is controllable by manipulating the various parameters prevailing within the system when operational. Accordingly the flow rate, pressure and quality, i.e. in the case of steam the dryness, of the transport fluid may be regulated to give the required intensity of shockwave. In this connection the intensity of the shockwave essentially relates to its degree of development within and across the passage and the mixing chamber. For example the shockwave may develop across the whole section or may only partially do so providing a central core that is open. The intensity of the shockwave may therefore be variable dependent upon the particular task the fluid mover has to perform. Furthermore the intensity of the shockwave may also be determined or defined by its position within or possibly without the passage or mixing chamber. As indicated supra the positioning of the shock wave may be manipulated in accordance with requirements and is not limited by the physical constraints of conventional ejectors since the pseudo-vena contracta is of variable dimension.

The supersonic shockwave constitutes in one aspect of its function a barrier through or across which fluid flow occurs in one direction only and in that respect may be regarded as a one-way valve, there being no designed possibility of backflow through the shockwave. Further, the steam condensation immediately leading up to the creation of a supersonic shockwave provides a self-induction mechanism whereby the transport fluid is drawn in by the very shockwave the fluid produces and accordingly is to some extent self-perpetuating when in operation. It is predominantly the position and intensity of the shockwave which dictates the pressure gradient obtained across the unit, which in turn defines the pressure and suction head and flow rate capabilities of the unit.

The passage may be of any convenient cross-sectional shape suitable for the particular application of the fluid mover. The passage shape may be circular, rectilinear or any intermediate shape, for example curvilinear.

Preferably the nozzle is located as close as possible to the projected surface of the working fluid in practice and in this respect a knife edge separation between the transport fluid or steam and the working fluid stream is of advantage in order to achieve the requisite degree of interaction. The angular orientation of the nozzle with respect to the working fluid stream is of importance and may be shallow.

In some embodiments of the present invention a series of nozzles is provided lengthwise of the passage and the geometry of the nozzles may vary from one to the other dependent upon the effect desired. For example, the angular orientation may vary one to the other. The nozzles may have differing geometries in order to afford different effects, i.e. different performance characteristics, with possibly differing parametric steam conditions. For example some nozzles may be operated for the purpose of heating whereas others are used simultaneously for mixing or disintegrating for example. Each nozzle will have a mixing chamber section downstream thereof. In the case where a series of nozzles is provided the number of operational nozzles is variable.

The nozzle may be of a form to correspond with the shape of the passage and thus for example a circular passage would advantageously be provided with an annular nozzle circumscribing it. The term 'annular' as used herein is deemed to embrace any configuration of nozzle or nozzles that circumscribes the passage of the fluid mover.

In the case of a rectilinear passage, which may have a large width to height ratio, nozzles would be provided at least on each transverse wall, but not necessarily on the side walls, although the invention optionally contemplates a full circumscription of the passage by the nozzle irrespective of shape.

The or each nozzle may be continuous or may be discontinuous in the form of a plurality of apertures, e.g. segmental, arranged in a circumscribing pattern that may be circular. In either case each aperture may be provided with helical vanes formed in order to give in practice a swirl to the flow of the transport fluid. As a further alternative the nozzle may circumscribe the passage in the form of a continuous helical scroll over a length of the passage, the nozzle aperture being formed in the wall of the passage.

The or each nozzle may be of a convergent-divergent geometry internally thereof, and in practice the nozzle is configured to give the supersonic flow of transport fluid within the passage. For a given steam condition, i.e. dryness, pressure and temperature, the nozzle is preferably configured to provide the highest velocity steam jet, the lowest pressure drop and the highest enthalpy.

For example only, and not by way of limitation, an optimum area ratio for the nozzle, namely exit area: throat area, lies in the range 1.75 and 7.5, with an included angle of less than 9°.

The or each nozzle is conveniently angled towards the flow since this occasions penetration of the working fluid and advantageously prevents both kinetic energy dissipation on the wall of the passage and premature condensation of the steam at the wall of the passage, where an adverse temperature differential prevails. The angular orientation of the nozzles is selected for optimum performance which is dependent inter alia on the nozzle orientation and the internal geometry of the mixing chamber. Further the angular orientation of the or each nozzle is selected to control the pseudo-convergent/divergent profile and the condensation shock wave position in accordance with the pressure and flow rates required from the fluid mover. Moreover, the creation of turbulence, governed inter alia by the angular orientation of the nozzle, is important to achieve optimum performance by dispersal of the working fluid in order to increase acceleration by momentum transfer. This aspect is of particular import when the fluid mover is employed as a pump. For example, and not by way of limitation, in the present invention it has been found that an angular orientation for the or each nozzle may lie in the range 0 to 30°.

A series of nozzles with respective mixing chamber sections associated therewith may be provided longitudinally of the passage and in this instance the nozzles may have different angular orientations, for example decreasing from the first nozzle in a downstream direction. Each nozzle may have a different function from the other or others, for example pumping, mixing, disintegrating, and may be selectively brought into operation in practice. Each nozzle may be configured to give the desired effects upon the working fluid. Further, in a multi-nozzle system by the introduction of the transport fluid, for example steam, phased heating may be achieved. This approach may be desirable to provide a gradual heating of the working fluid.

The mixing chamber geometry is determined by the desired and projected output performance and to match the designed steam conditions and nozzle geometry. In this respect it will be appreciated that there is a combinatory effect as between the various geometric features and their effect on performance, namely there is interaction between the various design and performance parameters having due regard to the defined function of the fluid mover.

At the location of the or each nozzle in the passage, the dimension of the passage is greater than either upstream or downstream thereof since this increase compensates for the additional volume of fluid introduced. However, the cross sectional area of the mixing chamber is always consonant with or greater than the cross sectional area of the passage whereby any material entering the passage meets no constriction. The cross-sectional area of the mixing chamber may vary with length and may have differing degrees of reduction along its length, i.e. the mixing chamber may taper at different angles at different points along its length. The mixing chamber tapers from the location of the or each nozzle and the taper ratio is selected such that the multiphase flow velocity and pressure distribution of the condensation shock wave is maintained at its optimum position. This point is found in the region of the throat of the mixing chamber, but the invention also foreshadows a different position, for example just after the throat. As heretofore indicated the intensity of the shockwave is controllable and coupled with its positioning will dictate its performance characteristics. As foreshadowed supra the supersonic shockwave may not extend across the whole of the cross-sectional dimension of the passage or mixing chamber and may resemble an annulus, for example it may be akin to a doughnut shape with a central relief. The regulation of the shockwave is a determinant of the performance of the fluid mover and is in turn dictated by its particular application.

The mixing chamber of the present invention may be of variable length in order to provide a control on the point at which collapse or implosion of the steam, i.e. condensation and pressure drop, occurs, thus affecting the extent of the supersonic shock wave and the performance of the fluid mover. The length of the mixing chamber is thus chosen to provide the optimum performance regarding momentum transfer. In some expressions of the invention the length may be adjustable in situ rather than predesigned in order to provide a measure of versatility. The collapse of the steam gives rise to an implosive force which also influences the entrapped working fluid within the circumscribing steam stream to the extent that a pinching effect takes place. Accordingly the steam collapse is focused and the working fluid induced thereby is directionalised.

A cowl may be provided downstream of the outlet from the passage in order to enhance the collapse effect and to harness the pressure and to accelerate an additional volume of the working fluid stream.

The fluid mover may also be provided with a fluid inlet nozzle, for example for the introduction of air or gas or indeed a liquid, provided in the passage intermediate the inlet and the outlet. The fluid nozzle may circumscribe the passage and may therefore be of annular form and may be located upstream and/or downstream of and/or coincident with the nozzle for the transport fluid or steam.

The fluid inlet or other inlets which may be provided in the passage may be used for the introduction of other gases or liquids or of other additives that may for example be treatment substances for the working fluid or may be particulates in powder or pulverulent form and used to seed or be mixed with the working fluid. The other inlets may additionally or alternatively be employed for the introduction of further working fluid. The fluids or other additives are entrained into the working fluid by the low pressure created within the unit, typically for example in the region of 0.2 bar. The fluids or additives can also be pressurised by an external means and pumped into the working fluid, if so required.

In a further embodiment of the present invention the fluid mover is disposed within a chamber provided with an inlet and an outlet, the inlet diverging to a central section of constant cross section in which the fluid mover is located and the chamber converging towards the outlet thereof. In this arrangement the working fluid is induced through the fluid mover and also around it within the confines of the chamber the outlet of which is no smaller than its inlet.

The fluid mover of the present invention may also be used in heating applications where the heat in the case of steam when used as the transport fluid is employed since necessarily the working fluid will receive heat from the steam. The heat of the steam may also have advantageous effects on the physical properties of the working fluid; for example the viscosity of the working fluid may be reduced.

According to a third aspect of the present invention a method of moving a working fluid includes presenting a fluid mover to the fluid, the mover having a straight-through passage of substantially constant cross section, applying a substantially circumscribing stream of a transport fluid to the passage through an annular nozzle, causing the collapse of the transport fluid thereof to create a region of low pressure thereby to induce working fluid flow through the passage (3), generating a supersonic shock wave within the passage downstream of the nozzle, inducing flow of the working fluid through the passage from an inlet to an outlet thereof, and modulating the shock wave to vary the working fluid discharge from the outlet.

The transport fluid is preferably a condensable fluid and may be a gas or vapour, for example steam.

According to a fourth aspect of the present invention a method of moving a working fluid includes presenting a fluid mover to the fluid, the mover having a straight-through passage of substantially constant cross section, applying a substantially circumscribing stream of steam to the passage through an annular nozzle, causing the collapse of the steam by virtue of condensation thereof to create a region of low pressure thereby to induce working fluid flow through the passage (3), generating a supersonic shock wave within the passage downstream of the nozzle, inducing flow of the working fluid through the passage from an inlet to an outlet thereof, modulating the shock wave to vary the working fluid discharge from the outlet.

The thermal capacity of the working fluid is generally sufficient to yield the desired result in terms of the condensation effect. However, in those instances where that capacity might be insufficient, the invention includes the step of introducing additional working fluid or another working fluid, e.g. water, at a location downstream of the introduction of the transport fluid, e.g. steam, in order to provide additional quenching of the steam to give the requisite result.

The method of the present invention involves the transfer of energy to the working fluid by a combination of heat, momentum and mass transfer as the transport fluid, e.g. steam, is accelerated to supersonic speeds and directed by the nozzle into the working or process fluid. The resulting mixture of the transport and working fluids is accelerated within the pseudo-convergent section before it decelerates as a result of shear losses, steam condensation, and mass transfer. It is the decelerative aspect of the invention that results in the generation of the supersonic shock wave.

In carrying out the method of the present invention the creation of a shock wave, plus control of its position and intensity, is occasioned by the design of the nozzle interacting with the setting of the desired parametric conditions, for example in the case of steam as the transport fluid the pressure, the dryness or steam quality, the temperature and the flow rate to achieve the required performance of the steam nozzle.

The fluid mover of the present invention may be employed in a variety of applications ranging from marine propulsion, where the mover is submersed within a body of fluid, namely the sea or lake or other body of water, to its use as a pump or mixer or aerator. In its application to pumping a variety of working fluids may be moved and may include liquids, liquids with solids in suspension, slurries, sludges and the like. It is an advantage of the straight-through passage of the mover that it can accommodate material that might find its way into the passage. The velocity and pressure generated within the passage and enhanced by the collapse of the transport fluid or steam are such as to ensure rapid movement through the passage. Such an advantage is also of particular import in the use of the fluid mover as a propulsion unit in the marine field where flotsam and jetsam can be a serious problem inhibiting the smooth running of more conventional propulsion units.

It has been found that the present invention by virtue of the shearing effect in combination with the shock wave affords a mechanism occasioning capability for breaking up any friable or readily disintegratable material that may have entered the passage, the combination of the shearing effect, namely an effect of shear dispersion and/or disassociation, and the shock wave having a disintegrating effect on the material.

The disintegrating effect of the supersonic shock wave assists in the transport of materials that would otherwise be regarded as difficult, for example slurries, sludges both primary and secondary, raw sewage or sewage sludge since the invention affords the capability of breaking up the solids for easier disposal. In a further example from the waste water industry this effect can be employed for disintegration of agglomerates and other particle size reduction in aerobic and anaerobic digesters. The combination of disintegration and heating of the sludge has an added benefit of increasing the biological activity of the sludge, thereby improving the generation of biogas within the digester. Any filter cake generated in the sewage treatment process, or indeed any other process, is also a candidate for disintegration using the fluid mover of the invention.

At the same time it has been found that the invention also has application to the destruction of harmful bacteria, for example *e-coli*, or the control of filamentous bulking in the waste water industry. The shearing mechanism afforded by the present invention coupled with the pressure gradient across the shock wave effectively destroys the bacteria in the fluid flow. The heat input of the transport fluid, usually steam, enhances this bacteria killing effect thereby providing for the sterilization of the working fluid. The sterilising effect could be enhanced further with the entrainment of chemicals or other additives which is mixed into the working fluid.

The present invention may also be used for the control and destruction of organisms. For example the present invention may be used for pumping and treatment of ballast water from marine vessels. The combination of the shearing mechanism, the shockwave and the heat input will destroy water borne organisms such as snails and artemia. This effect could be further enhanced with the introduction of air to the working fluid, thereby causing gas bubble trauma and/or gas saturation.

In the food industry for example, the present invention maybe used for the pasteurisation of potable and comestible products.

The invention further allows the treatment of liquids containing solids material of a size and flow rate greater than are possible with conventional equipment since the disintegrating action occurs across a larger cross section of passage than that available conventionally. Additionally any rogue material that may enter the fluid mover can be accommodated without damage since the fluid mover has little or no impedance.

The invention may also be used for mixing, dispersion or hydration and again the combination of the shearing mechanism and presence of the shock wave provides the mechanism for achieving the desired result. In this connection the fluid mover may be used for mixing one or more fluids, one or more fluids and solids in particulate form, for example powders. The fluids may be in liquid or gaseous form. It has been found that the use of the present invention when mixing liquid with a powder of particulate form a homogeneous mixture results, even when the powder is of difficult to wet material, for example Gum Tragacanth which is a thickening agent. This mechanism could also be used for example in the manufacture of paints, where powders and other additives, such as extenders, can be entrained, mixed and dispersed.

The treatment of the working fluid, for example heating, dosing, mixing, dispersing, emulsifying etc may occur in batch mode using at least one fluid mover or by way in an in-line or continuous configuration using one or more fluid movers as required.

A further use to which the present invention may be put is that of emulsification which is the formation of a suspension by mixing two or more liquids which are not soluble in each other, namely small droplets of one liquid (inner phase) are suspended in the other liquid(s) (outer phase). The present invention has achieved satisfactory emulsification in the absence of surfactant blends, although they may be used if so desired. It has been found that the present invention has achieved the emulsification of fat, oils and greases in water to a homogenised condition with a particle size down to 0.1 μm in a single pass through the fluid mover, without the use of a surfactant. In addition, due to the straight through nature of the invention, there is no limitation on the particle size that can be handled, allowing particle sizes up to the bore size of the unit whilst emulsification is taking place.

The fluid mover of the present invention may be used simply for transporting solids in a liquid carrier medium, for example paper pulp of up high consistency, particulates in water or other liquid, e.g. sand or gravel (5 mm pea shingle) in water of up to 80% solids. This high solids content capability is of particular importance in some applications, for example when used for moving radioactive material from collection tanks as part of nuclear decommissioning. There is less liquid to firstly separate from the solids and consequently less to dispose of safely.

A further example of solids handling capability is grain and split grain transport, where the present invention could also be utilised for separation of the husks.

Further the fluid mover may be employed for washing particulate materials of slurries to effect separation of the wanted from the waste elements. This usage has particular, but not exclusive, application to mineral dressing systems. This usage can also be applied to de-oiling of oil rich media.

I.e. separating the oil from other particles, for example oil sands, mill scale and oil spill from beaches.

Whilst there has been emphasis upon the use of a liquid working fluid, it is within the scope of the invention that the working fluid could be gaseous, for example air. In this connection, the fluid mover may be deployed as an extractor whereby the injection of the transport fluid, for example steam, effects induction of a gas for movement from one zone to another. One example of use in this way is to be found in fire fighting when smoke extraction at the scene of a fire is required. The present invention has the additional benefit of wetting or quenching of explosive or toxic atmospheres utilising either just the steam, or with additional entrained water and/or chemical additives. The latter configuration could be used for placing the explosive or toxic substances into solution for safe disposal.

Also for firefighting applications, the fluid mover may be deployed to draw air or another gas into its passage into which water or another fluid is introduced. The mixing and disintegrating functions of the invention may be exploited whereby the shearing effect mentioned above together with the pressure gradient across the shock wave give rise to conditions in which the water is atomised by the incoming transport fluid, e.g. steam. The atomisation of the water may be effected by its transport with the transport air and its passage through the supersonic shock wave and/or by a shearing effect. The atomisation effect as indicated above may be advantageously employed by the fire services, for example, when attending a fire or where there has been a leakage or escape of chemical or biological materials in liquid or gaseous form. The atomised spray provides a mist which effectively creates a blanket saturation of the prevailing atmosphere giving a thorough wetting result. The effect in the case of fire is to dampen down the combustion. In the case where chemical or biological materials are involved, the mist wets the materials and occasions their precipitation or neutralization. Additional treatment could be provided by entrainment of chemical or biological additives into the working fluid.

Once the fire is under control or the chemical or biological materials have been successfully neutralized, the fluid mover of the present invention may also be used as a means of collecting and discharging the liquid or gaseous waste from the site. This provides a further opportunity to neutralise the waste by virtue of the heat provided by the steam, and also allows further chemical or biological additives to be added and mixed with the fluids.

In this area of usage also lies another potential application in terms of foam generation for fire fighting purposes. A fluid mixture of water with a foaming agent, and possibly air, are mixed within the fluid mover using the transport fluid, e.g. steam, by virtue of a combination of the shearing effect and of the supersonic shock wave The straight through aspect of the invention has the additional benefit of offering very little flow restriction and therefore a negligible pressure drop, when a fluid is moved through it. This is of particular importance in applications where the fluid mover is located in a process pipe work and fluid is pumped through it when the fluid mover is turned off. In addition, the clear bore offers no impedance to cleaning 'pigs' or other similar devices which may be employed to clean the pipe work.

By way of example, four embodiments of a fluid mover in accordance with the present invention are described below with reference to the accompanying drawings in which:

BRIEF DESCRIPTION OF THE DRAWING FIGURES

Figure 2:
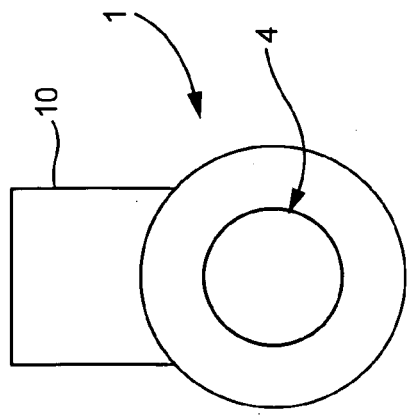
Figure 2:
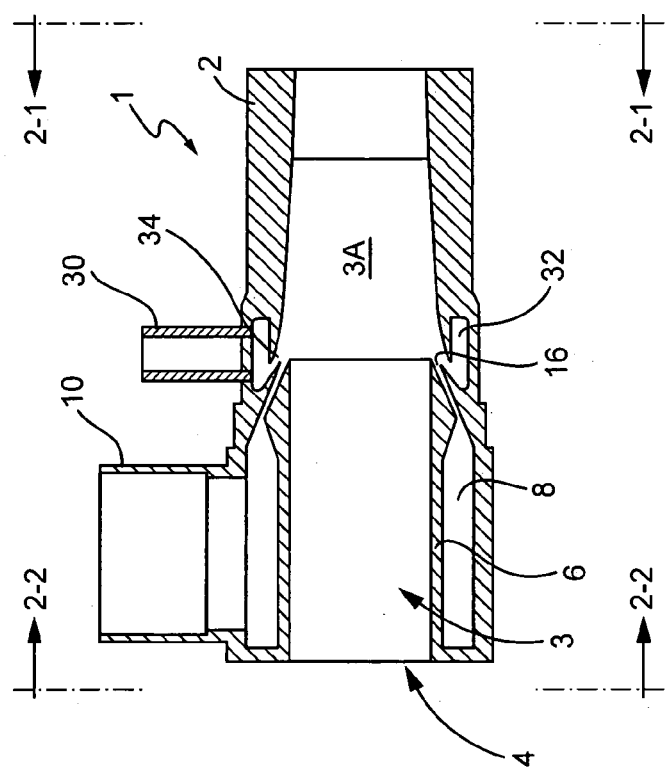
Figures 1, 2:
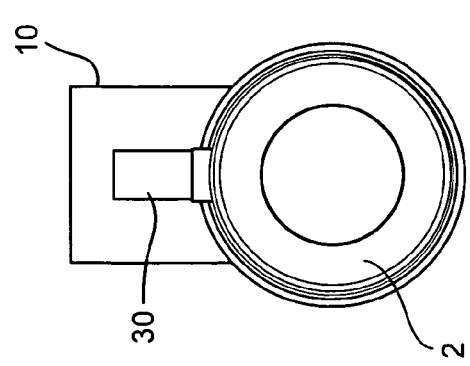

FIG. 1 is a cross sectional elevation of a first embodiment;

FIG. 2 is a cross sectional elevation of a second embodiment with end views shown as FIGS. 2-1 and 2-2 as taken along lines 2-1 and 2-2 therein, respectively;

FIG. 3 is a cross sectional elevation of a third embodiment with end views shown as FIGS. 3-1 and 3-2 as taken along lines 3-1 and 3-2 therein, respectively; and FIG. 4 is a cross sectional elevation of a third embodiment with end views shown as FIGS. 4-1 and 4-2 as taken along lines 4-1 and 4-2 therein, respectively.

Like numerals of reference have been used for like parts throughout the specification.

DETAILED DESCRIPTION OF THE INVENTION

Referring to FIG. 1 there is shown a fluid mover 1 comprising a housing 2 defining a passage 3 providing an inlet 4 and an outlet 5, the passage 3 being of substantially constant circular cross section.

The inlet 4 is formed at the front end of a protrusion 6 extending into the housing 2 and defining exteriorly thereof a plenum 8 for the introduction of a transport fluid, the plenum 8 being provided with an inlet 10. The protrusion 6 defines internally thereof part of the passage 3. The distal end 12 of the protrusion 6 remote from the inlet 4 is tapered on its relatively outer surface at 14 and defines an annular nozzle 16 between it and a correspondingly tapered part 18 of the inner wall of the housing 2, the nozzle 16 being in flow communication with the plenum 8. The nozzle 16 is so shaped as in use to give supersonic flow.

In operation the housing 2 in one application is disposed in a body of a working fluid (not shown), for example water, or the inlet 4 being connected to a source of a working or process fluid such as water. Introduction of the steam into the fluid mover 1 through the inlet 10 and plenum 8 causes a jet of steam to issue forth through the nozzle 16. The parametric characteristics of the steam are selected whereby in use a supersonic shock wave is generated within the passage 3 downstream of the nozzle 16 in a section of the passage operating as a mixing chamber (3A). In operation the shock wave is created in the mixing chamber (3A) and is maintained at an appropriate distance within mixing chamber (3A). The steam jet issuing from the nozzle occasions induction of the working fluid through the passage 3 which because of its constant dimension presents no obstacle to the flow. At some point determined by the steam and geometric conditions, and the rate of heat and mass transfer, the steam collapses or implodes and thus condenses causing a reduction in pressure. The steam condensation occurs immediately in front of the shockwave which is thus formed, which in turn creates a high pressure gradient which enhances the induction of fluid through the passage 3.

Additionally it has been observed that the collapse of the steam, which is part of the mechanism by which the invention functions, does not give rise to a tell-tale wake and therefore the physical fluid signature of the fluid mover is thus of low level.

FIG. 2 shows a second embodiment similar to that illustrated in FIG. 1 save that an inlet 30 and plenum 32 are provided in the housing 2, together with a further annular nozzle 34 formed at a location coincident with that of the nozzle 16. In this instance in use air is introduced to the nozzle 34 from the inlet 30 and the plenum 32 and thence to the passage 3 to aerate the flow whereby a three-phase condition is realised constituted by the liquid phase of the body of water, the steam and the air.

The use of air or another gas may assist in the suppression of cavitation thus reducing physical deterioration of the housing when it occurs near the wall of the housing. In this connection the suppression of cavitation has the beneficial effect of reducing noise levels and accordingly the sonic signature of the fluid mover is thus diminished. This attribute in practice would have benefits where the mover is to be used in its marine propulsion application, particularly when a low signal is desirable.

The performance of the present invention can be complimented with the choice of materials from which it is constructed. Although the chosen materials have to be suitable for the temperature, steam pressure and working fluid, there are no other restrictions on choice. For example, high temperature composites could be used to optimise the attenuation of noise for enhanced acoustic signal reduction in a marine application The nozzle 34 or another nozzle or nozzles may alternatively form the inlet for other fluids, or solids in flowable form such as a powder, for use in mixing or treatment purposes. For example, a further air nozzle may be provided in the passage to provide aeration of the working fluid if necessary. The placement of the further nozzle may be either upstream or downstream of the transport fluid nozzle or where more than one further nozzle is provided the placement may be both upstream and downstream dependent upon requirements. In another embodiment of the invention the nozzle 34 is used to introduce further working fluid or another fluid, for example water, in the event that the thermal capacity of the main working fluid flow may be insufficient to sustain the quenching of the steam to provide the requisite suction for the working fluid. This approach may be particularly applicable for liquids of low thermal capacity or those of relatively high viscosity where the addition of a further fluid such as water is required to substitute for any lack of quenching.

Referring now to FIG. 3 the fluid mover of FIG. 1 is provided with a frusto-conical cowl 40 adjacent the outlet 5 of the passage 3. Its disposition at this location allows a further concentration of the induction effect by virtue of the working fluid being drawn in not only through the inlet 4 but also through the annulus 42 formed between the outlet 5 and the internal wall of the cowl 40. A venturi effect is produced and thus affords a further acceleration of the flow through the combination of the housing and the cowl and thus the thrust is enhanced. The position of the cowl may be varied in order to give the desired effect.

With reference to FIG. 4, the embodiment of FIG. 1 is disposed centrally within a casing 50 having a diverging inlet portion 52 having an inlet opening 54, a central portion 56 of constant cross section, leading to a converging outlet portion 58 having an outlet opening 60. In use the inlet and outlet openings 54 and 60 are in flow communication with a body of a working fluid either therewithin or connected to a conduit. In operation the working fluid is drawn through the casing 50 with flow being induced around the housing 2 and also through the passage 3 of the mover which is of similar design to that shown in FIG. 1. The convergent portion 58 of the casing provides a means of enhancing the accelerative effect of the fluid mover and thus improves the thrust of the fluid flow. As an alternative to the specific configuration as shown in FIG. 4, the inlet portion 52 may display a shallower angle or indeed may be dimensionally coincident with the full bore 56.

EXAMPLE

By way of example only, we have designed a fluid mover (1) having a central passage (3A) bore of 47 mm for use at 5 bar gauge of steam with a dryness of 99%, the annular nozzle having an area ratio of 1.9 with an included angle of 5.7° and a throat gap of 1.34 mm. The angle at which the nozzle is orientated in relation to the axis of the flow passage (3) and that of the mixing chamber (3A) is 24°. The mixing chamber (3A) has a double taper starting at 8° and reducing to 3° included angle at 60% of its length, the length to diameter ratio being 2.13. It has been found that this configuration provides a fluid mover giving greater performance than conventional systems. For example the pumped flow rate of the working fluid is typically 40% to 100% higher than conventional systems, whilst simultaneously performing other functions such as heating, mixing etc.

The improved performance of the present invention has the additional benefit over conventional systems in requiring less steam to achieve a given performance, I.e. a lower proportion of steam is added to the working fluid. Typically, this is in the region of 1% by mass.

The present invention provides the means whereby the generation of a supersonic shock wave within the fluid mover and its extension therefrom with the attendant condensation of the transport fluid, namely steam, the thrust afforded is enhanced by virtue of the momentum transfer from the steam to the working fluid giving it added acceleration. The action of the supersonic shock wave is controllable by varying the geometry of the fluid mover and the parametric conditions of the transport fluid.

The present invention differs from the prior art as embodied particularly in Canadian Patent No 833 980 in that the positioning of the shock wave is not critical; although its positioning in the mixing chamber, equivalent to the conical inlet zone of Schutte and Koerting, is advantageous it may be generated at any desired position, supersonic velocity only occurring at the shock wave itself. Although the geometry of the present invention is of importance it is not dependent upon the use of the conventional 'venturi' configuration of a convergent inlet zone, a throat and a divergent outlet zone which characterises and is the essential geometry of the Schutte and Koerting jet pump. The Schutte and Koerting jet pump is specifically directed at the precise positioning of the shock wave to prevent spasmodic or erratic flow conditions.

In the present invention the supersonic velocity and the generation of the shock wave creates an accelerative effect which is of considerable advantage. This mode of operation is accordingly in sharp contrast to the Schutte and Koerting approach which teaches in precisely the opposite direction. It is to be noted that Schutte and Koerting regard such an accelerative effect to be deleterious in terms of a reduction in efficiency.

Indeed the Schutte and Koerting approach predicates the existence of a spasmodic flow by virtue of the hunting of the shock wave within the diffusor and the objective is to smooth out the flow. In contradistinction the present invention does not rely on precision location of the shock wave within the bounds of the apparatus in order for it to operate satisfactorily. Furthermore it would appear that the prior art shock wave would in practice extend across the whole of the diffusor section, and since the pumped fluid is gas this full section shock wave would be generated. As foreshadowed supra the shock wave of the present invention may not extend across the whole of the chamber cross section and may be constituted in a doughnut form with a central opening. Such variation in shock wave contour is entirely acceptable in the present invention and in certain applications may be particularly advantageous in terms of the shock wave becoming a threshold of momentum transfer at the point of steam condensation which itself creates a high pressure gradient, the implosive and inductive effect thereof providing the intended acceleration of the fluids.

The present invention is thus versatile in contrast with Schutte and Koerting in that as aforesaid the shock wave positioning is not critical, thus enabling a broader range of operating parameters and indeed applications particularly with regard to the types of fluid throughput. The versatility is achieved by the generation of the pseudo-convergent/divergent sections which afford a flexibility of operation that cannot be attained by the conventional techniques as exemplified by Schutte and Koerting. The flexible boundary within the flow regime is controllable by the adjustment of the parameters of the transport fluid, viz. the steam pressure and/or flow rate.

It is this versatility that allows the present invention to be applied in many different applications over a wide range of operating conditions. Furthermore the shape of the fluid mover may be of any convenient form suitable for the particular application. Thus the fluid mover may be circular, curvilinear or rectilinear, to facilitate matching of the fluid mover to the specific application or size scaling. Size scaling is important in terms of being able readily to accommodate differing designed capacities in contrast to conventional equipment, e.g. an ejector, where significant difficulty may be encountered by virtue of the physical restraints imposed by the very nature of its configuration. It is also the case that at the point of shock wave generation a disintegrating effect is realised and for certain applications, for example those in which fluid/solids mixtures are to be pumped this effect is advantageous in facilitating and smoothing flow patterns and indeed in enhancing the performance of the pumping mechanism. Additionally in certain applications disintegration of the solids element of the mixtures is an objective and of prime consideration, and the shock wave front effectively breaks down the solids into discrete pieces. The advantage of the present invention in this respect is that it affords a duality of function in terms of smoothing flow and of fulfilling a process application requirement.

Emulsification is also possible with the deployment of the fluid mover of the present invention on a once-through basis this obviating the need for multi-stage processing. In this context also the mixing of different liquids and/or solids is enhanced by the fluid mover by virtue of the combination of the shearing mechanism and its supersonic shock wave which effects the necessary intimacy between the components being brought together as exemplified heretofore.

The heating of fluids and/or solids can be effected by the use of the present invention by virtue of the steam input as the transport fluid and of course in this respect the invention has multi-capability in terms of being able to pump, heat, mix and disintegrate, the relevant adjustment being effected by the modulation of the steam characteristics and thus the variation of the shock wave positioning.

The use of steam is also important for example in the food industry where 'cleaning in place' (known as 'CIP') of conduits used for the transport of fluid ingredients is necessary. The steam has a scavenging or scouring action on the conduit walls and a benefit of the present invention is that it does not possess any intricate internal formations that could constitute areas of deposition where contaminating matter may accumulate. In other words the fluid mover of the invention presents a clear internal profile free of sharp changes that could harbour contaminants.

The fluid mover is capable of operating with working fluid at higher temperatures than those associated with conventional equipment since for a given steam input the volume throughput of the working fluid is much greater and thus the working fluid provides for a greater thermal capacity for condensing the steam.

The fluid mover is accordingly advantageous not only in the treatment of the working fluid but also in the cleansing application mentioned above in that there is a sterilising effect. The operation of sterilising plant is known as 'sterilising in place' (known as 'SIP'). The invention can thus be used in dual mode to clean and to sterilise and thus in certain applications pasteurise the working fluid, and thus operates as an in situ steam cleaner without the need for auxiliary plant. The added advantage is that the fluid mover is itself multi-functional and thus operates as a pump simultaneously with its operation as a cleaning mechanism. The sterilising of equipment with which the fluid mover is associated may be effected in batch or continuous mode. A cleaning agent, which is typically caustic in most industries, may be pumped through the equipment by means of the fluid mover without the requirement of an additional pump. The fluid mover has an advantage over conventional pumps for this application due to its lack of moving parts and delicate dynamic seals, which are often sensitive to a caustic environment.

The present invention thus has wide applicability in industries of diverse character ranging from the food industry at one end of the chain to waste disposal at the other end.

As foreshadowed in the foregoing description the present invention also has potential application as a firefighting tool in terms of providing a means of smoke extraction having the advantage of both damping and precipitating the gas-borne particles in the smoke. It may also be used to atomise water thereby producing a fine mist for application to fires to suppress combustion. Additionally, the fluid mover may be applied to foam making again for use in firefighting, the invention being used for mixing of the foaming agent with water and possibly air.

As has been indicated above, the present invention possesses a number of advantages in its operational mode and in the various applications to which it is relevant. For example the 'straight-through' nature of the fluid mover having a substantially constant cross section, with the bore diameter never reducing to less than the inlet, means that not only will fluids containing solids be easily handleable but also any rogue material will be swept through the mover without impedance. The fluid mover of the present invention is tolerant of a wide range of particulate sizes and is thus not limited as are conventional ejectors by the restrictive nature of their physical convergent/divergent sections. The fluid mover provides flexibility by virtue of the pseudo-convergent/divergent sections to accommodate any variations in throughput material size.

The suppression of cavitation effected by aeration of the working fluid which also reduces surface friction losses also diminishes its sonic signature and accordingly benefits accrue in terms of the application of the invention in the field of marine propulsion. The suppression of cavitation also has benefits in obviating the cause its deleterious physical effects, such as pitting.

In the case where only two phases are present, the energy transfer from the steam to the working fluid only produces a transient wake and accordingly the physical flow signature of the mover is small and short-lived. Again benefits are derived from such a mechanism.

The present invention thus affords wide applicability with improved performance over the prior art proposals in the field of fluid movers.

It is to be understood that the expression 'aeration' as used herein is intended to cover the introduction of air or other gas into the working fluid.

The invention claimed is:

1. A fluid mover comprising:
    a hollow body provided with a straight-through passage of substantially constant cross-section, said passage having an inlet end and an outlet end for the entry and discharge respectively of a working fluid,
    a transport fluid nozzle substantially circumscribing and opening into said passage intermediate the inlet and outlet ends thereof,
    a transport fluid inlet communicating with the transport fluid nozzle for the introduction of a transport fluid, and
    a mixing chamber being formed within the passage downstream of the transport fluid nozzle, the transport fluid nozzle being of convergent-divergent geometry internally thereof such as in use to provide for the generation of supersonic flow of the transport fluid therein, and the transport fluid nozzle and mixing chamber being so disposed and configured that in use a dispersed droplet flow regime and a supersonic shockwave are created within the mixing chamber by the introduction of the transport fluid through the transport fluid nozzle and subsequent condensation thereof and whereby a pseudo convergent-divergent section is created in the working fluid flow in the mixing chamber by the introduction of the transport fluid through the transport fluid nozzle.

2. A fluid mover as in claim 1, wherein the transport fluid is steam and the transport fluid nozzle is a steam nozzle, and wherein the nozzle and mixing chamber being so disposed and configured that in use a dispersed droplet flow regime and a supersonic shockwave are created within the mixing chamber by the introduction of the transport fluid through the transport fluid nozzle and subsequent condensation thereof and whereby a pseudo convergent-divergent section is created in the working fluid flow in the mixing chamber by the introduction of the transport fluid through the transport fluid nozzle.

3. A fluid mover according to claim 1 wherein the shape of the passage may be circular, curvilinear or rectilinear.

4. A fluid mover according to claim 1 wherein the transport fluid nozzle is disposed in such manner as in use to be in close adjacency to the projected surface of the working fluid.

5. A fluid mover according to claim 4 further comprising a knife-edge separation between the transport fluid and the working fluid.

6. A fluid mover according to claim 1 wherein the transport fluid nozzle is annular.

7. A fluid mover according to claim 6 wherein the transport fluid nozzle includes a single aperture.

8. A fluid mover according to claim 1 wherein the transport fluid nozzle is configured to give the highest velocity steam jet, the lowest pressure drop and the highest enthalpy.

9. A fluid mover according to claim 1 wherein the transport fluid nozzle is angled towards the passage.

10. A fluid mover according to claim 1 which comprises a plurality of transport fluid nozzles spaced apart longitudinally of the passage, each said transport fluid nozzle being provided with a mixing chamber section downstream thereof.

11. A fluid mover according to claim 10 wherein the transport fluid nozzles are at different locations along the passage and have differing geometries.

12. A fluid mover according to claim 1 further comprising at least one secondary nozzle intermediate the inlet and the outlet ends of the passage (3).

13. A fluid mover according to claim 12 wherein said at least one secondary nozzle is located upstream and/or downstream of the transport fluid nozzle.

14. A fluid mover according to claim 1 wherein the cross sectional dimension of the passage at the location of the transport fluid nozzle is greater than that either upstream or downstream thereof.

15. A fluid mover according to claim 1 wherein the cross-sectional area of the mixing chamber is equal to or greater than that of the passage.

16. A fluid mover according to claim 15 wherein the cross-sectional area of the mixing chamber varies with its length.

17. A fluid mover according to claim 16 wherein the degree of variation differs along the length of the mixing chamber.

18. A fluid mover according to claim 1 further comprising a cowl downstream of the outlet from the passage.

19. A method of moving a working fluid comprising the steps of:
(a) presenting a fluid mover to the fluid, the mover having a straight-through passage of substantially constant cross section,
(b) applying a substantially circumscribing stream of a transport fluid to the passage through an annular transport fluid nozzle thereby creating a pseudo-convergent/divergent section in the working fluid flow,
(c) causing the collapse of the transport fluid thereby to create a region of low pressure to induce flow of the working fluid through the passage,
(d) generating a dispersed droplet flow regime and a supersonic shock wave within a mixing chamber downstream of the transport fluid nozzle,
(e) inducing flow of the working fluid through the passage from an inlet end to an outlet end thereof, and
(f) modulating the shock wave to vary the working fluid discharge from the outlet end.

20. A method as in claim 19, wherein steam is the transport fluid.

21. A method according to claim 20 which comprises varying the steam characteristics of pressure, flow rate, dryness and/or temperature to provide the required performance of the steam nozzle.

22. A method according to claim 20 comprising the step of introducing additional fluid into the passage downstream of the transport fluid nozzle to enhance the condensation of the steam.

23. A method according to claim 22 wherein the additional fluid is working fluid.

24. A method according to claim 22 wherein the additional fluid is water.

25. A method of moving a working fluid according to claim 20 comprising the step of introducing at least one additional liquid into the passage upstream or downstream of the nozzle, and wherein the working fluid is air, and the additional liquid is water whereby the water is atomised upon encountering the shearing effect of the steam and the supersonic shock wave thereby to generate a mist.

26. A method according to claim 19 wherein the pseudo-convergent/divergent section in the fluid flow presents a flexible boundary lying between the working fluid and the wall of the passage.

27. A method according to claim 19 further comprising the step of introducing at least one additional fluid and/or solid into the passage upstream or downstream of the transport fluid nozzle.

28. A method according to claim 27 wherein at least one additional fluid in the form of one or more liquids is introduced into the passage.

29. A method according to claim 27 wherein at least one additional solid in particulate form is introduced into the passage.

30. A method according to claim 27 wherein at least one additional solid in pulverulent form is introduced into the passage.

31. A method according to claim 27 wherein at least one additional solid in gelatinous and/or glutinous form is introduced into the passage.

32. A method according to claim 19 wherein the working fluid is a liquid.

33. A method according to claim 32 wherein the working fluid includes a foaming agent.

34. A method according to claim 19 wherein the working fluid is a mixture of a fluid and solids material.

35. A method according to claim 34 wherein the mixture is a sludge or slurry.

36. A method according to claim 34 wherein the solids material is particulate in form.

37. A method according to claim 34 wherein the solids material is in pulverulent form.

38. A method according to claim 34 wherein the solids material is a fatty substance, oil or grease.

39. A method of moving a working fluid according to claim 38 wherein the fatty substance, oil or grease of the working fluid is emulsified thereby.

40. A method of moving a working fluid according to claim 34 which comprises the step of allowing the solids material to disintegrate and/or mix within the fluid.

41. A method of moving a working fluid according to claim 40, which comprises the step of introducing the solids material into the fluid through at least one secondary nozzle.

42. A method according to claim 19 wherein the working fluid is gaseous.

43. A method according to claim 42 wherein the gaseous working fluid is air.

44. A method according to claim 42 wherein the gaseous working fluid is smoke.

45. A method moving a working fluid according to claim 19 wherein the working fluid is heated thereby.

* * * * *